United States Patent [19]

Lepp et al.

[11] 4,142,845

[45] Mar. 6, 1979

[54] DIALYSIS PUMP SYSTEM HAVING OVER-CENTER CAM TRACKS TO LOCK ROLLERS AGAINST TUBING

[76] Inventors: William A. Lepp, 322 Waterloo St.; Jules O. Legal, 89 Elm Park Rd., both of Winnipeg, Manitoba, Canada

[21] Appl. No.: 836,960

[22] Filed: Sep. 27, 1977

Related U.S. Application Data

[63] Continuation-in-part of Ser. No. 659,759, Feb. 20, 1976, abandoned.

[51] Int. Cl.² .................... F04B 43/08; F04B 43/12; F04B 45/06
[52] U.S. Cl. .................................... 417/477; 251/9
[58] Field of Search ................ 417/477, 476, 475; 128/214 E, 214 F, DIG. 12; 251/9

[56] References Cited

U.S. PATENT DOCUMENTS

| | | | |
|---|---|---|---|
| 1,703,361 | 2/1929 | Pohl | 417/477 |
| 2,314,281 | 3/1943 | Knott | 417/477 |
| 3,192,863 | 7/1965 | Vadot | 417/477 |
| 3,300,562 | 1/1967 | Moore | 251/9 |
| 3,335,753 | 8/1967 | Kiser | 251/9 |
| 3,447,478 | 6/1969 | Clemens | 417/477 |
| 3,762,836 | 10/1973 | DeVries | 417/477 |
| 3,836,287 | 9/1974 | Grosholz et al. | 417/477 |
| 3,865,134 | 2/1975 | Holcomb | 251/9 |
| 3,938,909 | 2/1976 | Willock | 417/477 |
| 3,960,466 | 6/1976 | Taylor | 417/477 |
| 4,070,725 | 1/1978 | Austin et al. | 417/477 |

FOREIGN PATENT DOCUMENTS

1141883 2/1969 United Kingdom .................... 251/9

*Primary Examiner*—Carlton R. Croyle
*Assistant Examiner*—Thomas I. Ross
*Attorney, Agent, or Firm*—Stanley G. Ade

[57] ABSTRACT

A source of power rotates a drive shaft upon which a pair of rollers are mounted. The rollers rotate in a recess and collapse an undialysed blood carrying tube against a wall thus causing a pumping action. When used with a single needle dialysis system, an occluding pin assembly intermittently clamps off the dialysed blood carrying tube as said source of power is interrupted in rotation thus permitting the device to be used with a conventional single needle assembly. By rotating a cylindrical member upon the upper end of the drive shaft, the rollers can be retracted from adjacent the wall against which the undialysed blood carrying tube rests thus facilitating the engagement and disengagement of the undialysed blood carrying tube with the device. Inasmuch as the wall thickness of such tubes often varies, between tubing produced by different manufacturers, means are provided to adjust the spatial relationship of the pump rollers with the wall against which the tube is pressed during the pumping action. A hinged lid is provided which, when closed, enables power to flow to the motor. This lid also includes means to retain the tubes in position during the operation of the device. The speed of the pump can be varied within limits and the timing sequence of the pump can also be varied within limits. Means are provided to disable the occluding pin assembly when the device is used with a double needle dialysis system.

17 Claims, 16 Drawing Figures

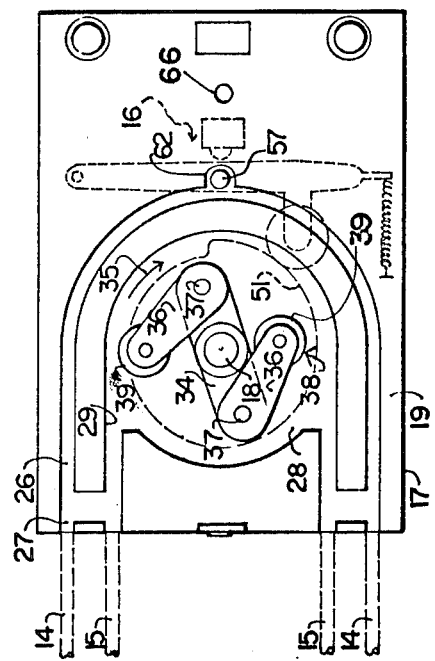

DIALYSIS PUMP SYSTEM HAVING OVER-CENTER CAM TRACKS TO LOCK ROLLERS AGAINST TUBING

BACKGROUND OF THE INVENTION

This invention is a continuation-in-part application of Ser. No: 659,759, filed Feb. 20th, 1976, now abandoned, and relates to new and useful improvements in dialysis pumps adapted for use primarily with conventional dialysis machines utilizing the single or double needle dialysis systems.

Such machines require an occluding assembly for use with a single needle system. These occluders are usually separate from the pump and may incorporate a pressure monitor which operates the occluder. Such devices are unsatisfactory in use and are therefore undesirable.

The present invention utilizes a roller type peristaltic pump with a mechanical occluder incorporated therewith and means are provided to engage or disengage the occluder depending upon whether the pump is being used with a single needle or double needle system respectively.

Most peristaltic pumps require the manual engagement of a flexible tube within the pump so that a pair of rollers can rotate against the tube pressing same against a wall to form the peristaltic pumping action.

Two principal disadvantages are inherent with conventional peristaltic pumps. Firstly, it is difficult for an operator to engage the tube between the rollers and the wall due to the close proximity of the rollers with the wall which is, of course, required to give the pumping action. Secondly, the wall thicknesses of the tubing may vary from one manufacturer to another so that if a length of tubing having a relatively thick wall is used, there is a danger that the erythrocytes of the blood being pumped, may be damaged. Conversely, if the wall thickness is less than normal than the pumping action may be inefficient. This is because no adjustment is provided in conventional peristaltic pumps, to vary the distance between the rollers and the wall against which the tubing is squeezed during the pumping action.

SUMMARY OF THE INVENTION

The present invention overcomes these disadvantages firstly by providing a relatively simple manually operated device whereby the rollers can be withdrawn clear of the wall for engagement and disengagement of the tubing whereupon the rollers can be moved to the operating position.

Secondly, means are provided to adjust, within limits, the distance between the periphery of the rollers and the wall against which the tubing is squeezed during the peristaltic pumping action.

The principal object and essence of the invention is to provide a dialysis pump, which includes a built in occluder assembly, and which can be used as part of a single or double needle dialysis system. In this regard, means are provided to enable the occluder assembly when the device is used as part of a single needle system and to disable the occluder assembly when used as part of a double needle system.

A further object of the invention is to provide a dialysis pump which includes means to manually retract the rollers from the wall in order to facilitate the engagement of the tubing within the pump.

Another object of the invention is to provide a device of the character herewithin described in which the distance between the pump rollers and the wall can be varied within limits.

Yet another object of the invention is to provide a device of the character herewithin described in which the hinged lid is adapted to hold both flexible tubes in position when the tubes are installed within the device.

Another object of the invention is to provide a device of the character herewithin described in which the pump will not operate until the lid or cover is securely closed.

A still further object of the invention is to provide a device of the character herewithin described which includes a simply operated occluder assembly, the timing of which may be controlled within limits and which is always correctly related to the timing of the operation.

Yet another object of the invention is to provide a device of the character herewithin described in which the speed of rotation of the pump can be controlled within limits.

A yet further object of the invention is to provide a device of the character herewithin described which although designed primarily for use with a single needle system, can be used with a dual needle system if desired, through the use of a simple control on the device which can disable the occluder assembly.

A still further object of the invention is to provide a device of the character herewithin described which is simple in construction, economical in manufacture and otherwise well suited to the purpose for which it is designed.

With the foregoing in view, and other advantages as will become apparent to those skilled in the art to which this invention relates as this specification proceeds, our invention consists essentially in the arrangement and construction of parts all as hereinafter more particularly described, reference being had to the accompanying drawings in which:

DESCRIPTION OF THE DRAWINGS

FIG. 1 is a top plan view of the device with the cover in the open position.

FIG. 2 is a side elevation of FIG. 1.

FIG. 3 is a top plan view of the device with the cover and roller retracting member removed for clarity.

FIG. 4 is a vertical cross sectional view of FIG. 3 substantially along the lines 4—4 of FIG. 1.

In the drawings like characters of reference indicate corresponding parts in the different figures.

BRIEF DESCRIPTION

In single needle dialysis, the connection from the patient to the dialysis system may be through a single cannulation of an A-V fistula, a bovine graft, an indwelling catheter or a large vein or artery. Connected to this entry close to the patient is the common leg of a "Y" fitting, while connected to the two branches of the "Y", are two plastic tubes. These tubes are the same as those used in the more conventional dual needle system of dialysis where blood is withdrawn from an artery through a tube called the arterial tube and the blood is pumped through a dialyser and returned to a vein through another tube called a venous tube.

These terms are not technically correct when describing a single needle system for the common vessel can be either an artery or a vein so that in the present application, the tubes are referred to as an undialysed blood carrying tube and a dialysed blood carrying tube. The undialysed blood carrying tube refers to the plastic tubing through which blood is withdrawn from a patient and the dialysed blood carrying tube refers to the plastic tubing through which blood is returned to the patient.

In the dual needle system, blood is pumped continuously from the patient through a dialyser and back into the patient.

In a single needle system, a relatively small volume of blood is drawn from the patient and pumped through the undialysed blood carrying tube into a dialyser. The return line from the dialyser, namely the dialysed blood carrying tube, is clamped off during this phase resulting in pressure building up within the dialyser.

At the end of this phase the undialysed blood carrying tube is clamped off and at the same instant, the dialysed blood carrying tube is opened. Pressure within the dialyser forces dialysed blood back into the patient and during this phase the pump is at rest.

All systems utilizing a single needle arrangement employ these same basic principles and although the present invention has been designed specifically for use with single needle dialysis, nevertheless it can be changed readily to be utilized with the more conventional double needle dialysis systems by disabling the occluder assembly.

DETAILED DESCRIPTION

Figure 7:
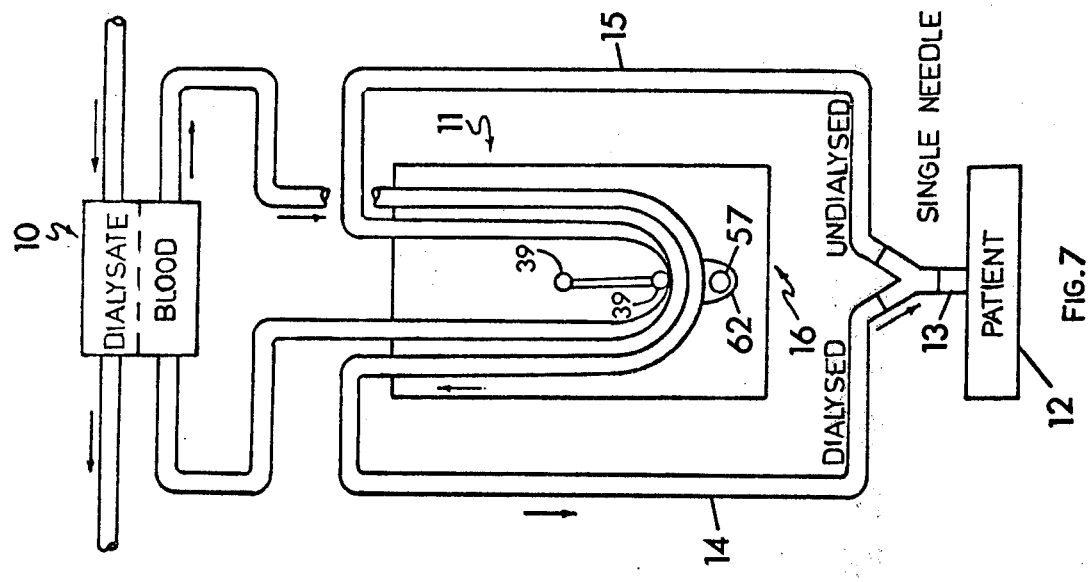
FIG. 7 is a view similar to FIG. 6 but with the occluder in the tube open position and the pump in the stationary mode.
Figure 6:
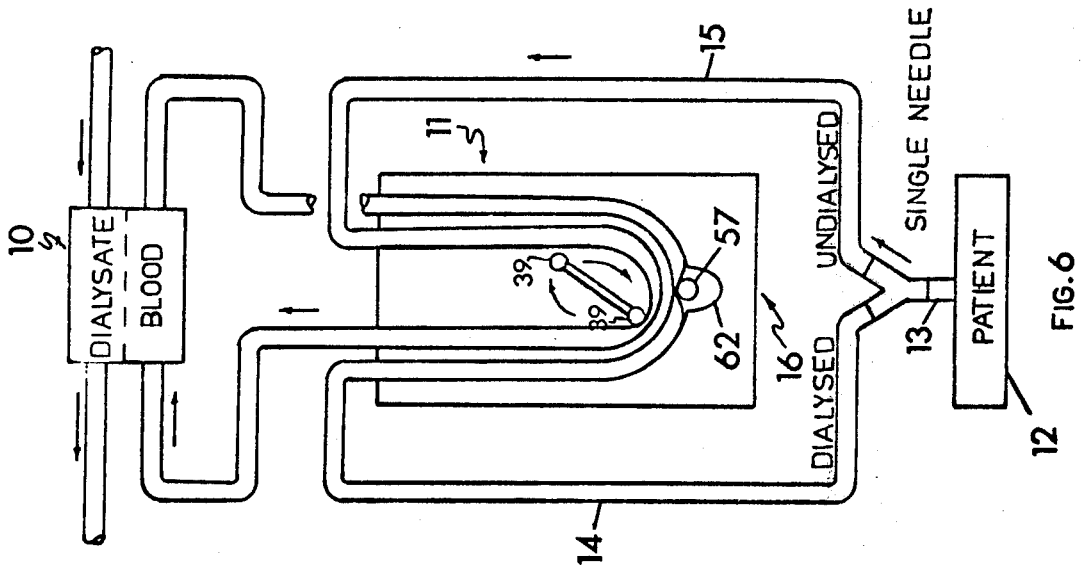
FIG. 6 is a schematic view of the device with the occluder in the tube closed position and the pump in the rotating mode.

Proceeding therefore to describe the invention in detail, reference should first be made to FIGS. 6 and 7 in which reference character 10 illustrates schematically, a dialyser unit with 11 indicating the dialyser pump of the instant invention. The patient is indicated by reference character 12 and the conventional single needle entry to the patient is shown by reference character 13.

Reference character 14 illustrates schematically, a dialysed blood carrying tube and 15, an undialysed blood carrying tube and the routing of these tubes through the pump and to the dialyser is clearly indicated by the arrows attached to the tubes.

FIG. 6 shows the pump in the operating mode rotating clockwise with an occluder assembly 16 in position to close off the dialysed blood carrying tube within the pump unit.

Under these circumstances, the rotation of the pump withdraws a quantity of blood from the patient and feeds same to the dialyser 10.

At a pre-determined point, the pump ceases rotation and the occluder is released as indicated in FIG. 7 so that the pressure built up within the dialyser due to the pumping action, forces the dialysed blood back to the patient through the dialysed blood carrying tube 14, it being understood that undialysed blood carrying tube is clamped off due to the fact that the pump is not rotating in this phase.

The pump unit collectively designated 11 is contained within a casing 17 within which is contained a source of power (not illustrated) in the form of an electric motor and the appropriate gearing required to rotate a drive shaft 18 which extends upwardly through an upper plate 19 situated at the upper side of the casing. In this regard, means are provided to control the pump speed and are shown schematically by reference character 20 and merely take the form of a suitable control operating the electric motor in a conventional manner.

Power is supplied from a source of electrical energy in the usual way and controlled by means of an off-on switch 21 also provided on the upper side of the panel.

A hinged lid 22 is provided hinged transversely to the upper side of the casing as indicated by reference character 23 and this hinged lid, when moved to the closed position, clips underneath a retaining latch 24 extending upwardly from the front wall 25 of the casing thus holding the lid firmly in the closed position. An interlock (not illustrated) is provided between this lid and casing to ensure that power only flows to the electric motor when the lid is closed and locked.

An arcuately curved channel 26 is formed within the upper panel 19, said channel having ends which open out onto the upper side of the front wall 25 of the casing and being indicated by reference character 27. This permits the aforementioned dialysed blood carrying tube 14 to be laid around this channel or groove and to extend between the single needle 13 and the dialyser machine as shown schematically in FIGS. 6 and 7.

The central area 28 of the upper plate is recessed and this recess is defined by a vertical wall 29 which is radially curved and which also opens out onto the upper side of the front panel 25 as indicated by reference character 30 and the aforementioned undialysed blood carrying tube 15 may be laid within this recess against the curved wall 29, once again as illustrated schematically in FIGS. 6 and 7, and this tubing is of course connected between the dialyser and the single needle 13 as clearly shown.

The upstanding portion 31 between the channel 26 and the recessed area 28, is cut away as indicated by reference character 32, adjacent the front side of the upper plate 19 and these cut away portions receive transversely situated relatively soft and resilient pads 32 secured to the underside of the lid or cover 22 to adjacent the front edge 33 thereof so that when the lid or cover is in the closed position, these pads engage through the portions 32 and span the tubes 14 and 15 on both sides of the device and assist in holding the tubes firmly in position during the operation of the pump.

The pump utilized is a peristaltic type pump driven by the aforementioned drive shaft 18.

A cross bar or rotor 34 is keyed or otherwise secured to the drive shaft and extends transversely of the upper end and is rotated by the drive shaft in the direction of arrow 35 (see FIG. 3). A link 36 is pivotally secured adjacent each end of the cross bar, by means of pivot pins 37 and these links are in trailing relationship to the cross bar as clearly shown in FIG. 3.

Figure 13:
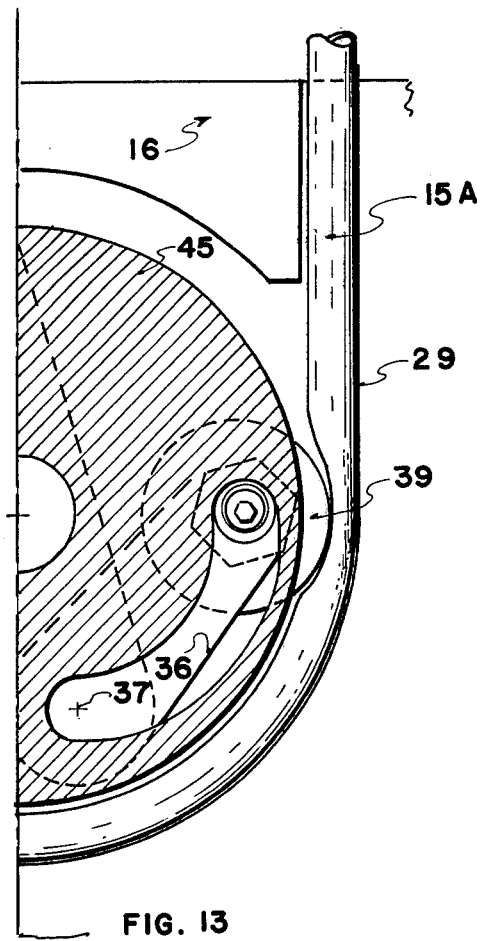
FIG. 13 is a fragmentary view similar to FIG. 12, but showing the position of the roller used with a relatively thick walled tube.
Figure 14:
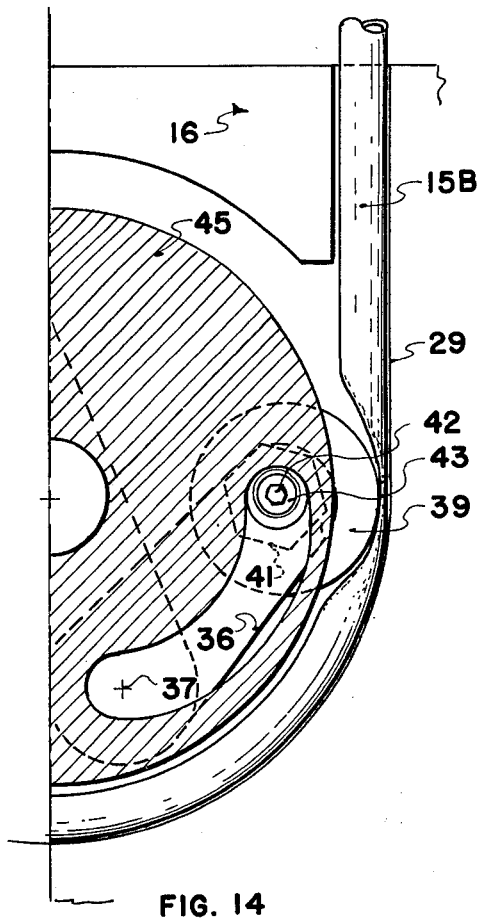
FIG. 14 is a view similar to FIG. 13 but showing the roller in use with a relatively thin walled tube.

Reference to FIGS. 13 and 14 show that a roller assembly 38 is mounted adjacent the outer ends of each of the links 36, said roller assembly including a roller 39 journalled by means of roller or ball bearings 39A, upon a small mounting sleeve 40 having a hexagonal or similar configuration upper shoulder or stub portion 41. Fastening means such as an Allan screw 42 secures the assembly to the link 36 through a pin or slot engaging sleeve 43 on the upper side of the link 36. The sleeve 40 is eccentric so that if the Allan screw 42 is slackened off, the sleeve may be rotated by a flat open ended wrench due to the provision of the hexagonal portion 41, thus shifting the axis of rotation of the roller 39, laterally, relative to the wall 29. This fine adjustment is provided so that the individual rollers can be adjusted within limits to ensure that sufficient pressure is provided by the rollers upon the tubing 15, in order to close off the tubing as the rollers rotate yet to ensure that excessive pressure is not applied which may have the effect of damaging the blood erythrocytes. Access to the Allan screw is through appropriate holes 50 through cap or disc 45 hereinafter to be described.

Figure 15:
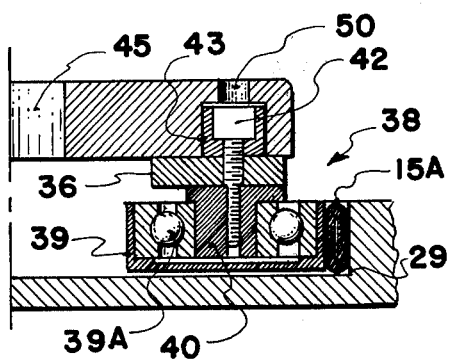
FIG. 15 is a fragmentary front elevation of FIG. 13 sectioned to show the interior thereof.
Figure 16:
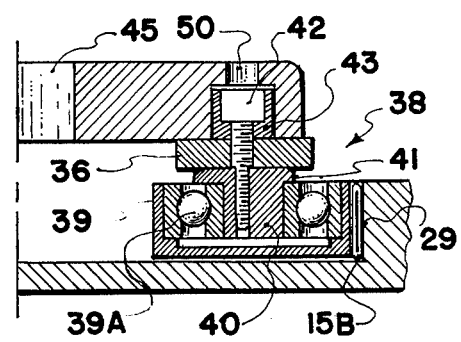
FIG. 16 is a view similar to FIG. 15 but showing a front elevation of FIG. 14.

FIGS. 13 and 15 illustrate an exaggerated heavy wall tube 15A and FIGS. 14 and 16 illustrate an exaggerated thin wall tube 15B. Once the proper distance has been determined, a wrench is used to lock the mounting stub 41 by tightening Allan screw 42. It is unlikely any further adjustment shall be required unless a different type of tube set is used.

A simple test may be provided to adjust these rollers relative to the wall 29 utilizing a water column connected to the tubing 15 and adjusting the rollers until the flow of water just ceases.

The adjustment of these rollers relative to the wall 29 is an important feature of the present invention.

As mentioned above, the Allan screw 42 also holds into position, a small sleeve 43 on the upper end thereof which extends upwardly from the upper side of link 36, the purpose of which will hereinafter become apparent.

In conventional peristaltic machines, the roller assemblies are normally fixed relative to the drive shaft and cannot be pivoted as in the present invention. This means that there is relatively little clearance between the periphery of the rollers and the wall against which they press the tube during the pumping action thus making it extremely difficult to install or engage the undialysed blood carrying tube between the rollers and the wall.

In the present device, the pivotal mounting of the rollers in conjunction with the assembly collectively designated 44, enable the tubing to be engaged and disengaged readily and easily.

Near each end of rotor 34 is an axis about which the links 36 hinge freely in trailing relationship. At the opposite end of these links is another axis through which the pumping rollers 39 rotate. The distance between the rollers 39 and the center of the rotor 34 is determined by a manually adjustable disc 45 forming part of an assembly 44.

Assembly 44, in the present embodiment, includes a cylindrical finger grasping cap or disc 45 freely mounted for rotation upon the upper end of drive shaft 18 by means of fastener 46.

Figure 12:
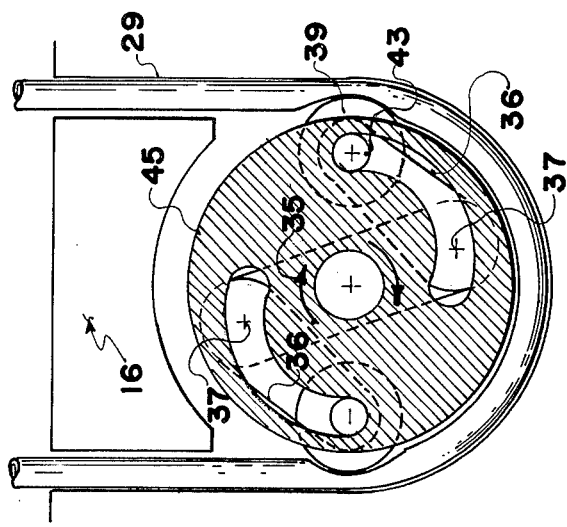
FIG. 12 is a view similar to FIG. 11 but showing the roller assembly fully extended.
Figure 11:
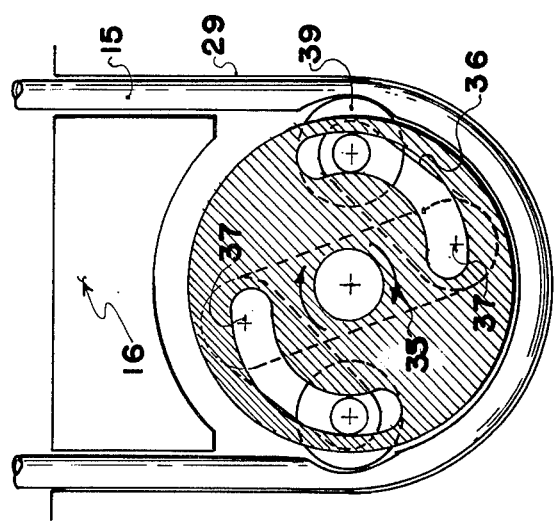
FIG. 11 is a view similar to FIG. 10 but showing the roller assembly partially extended.
Figure 10:
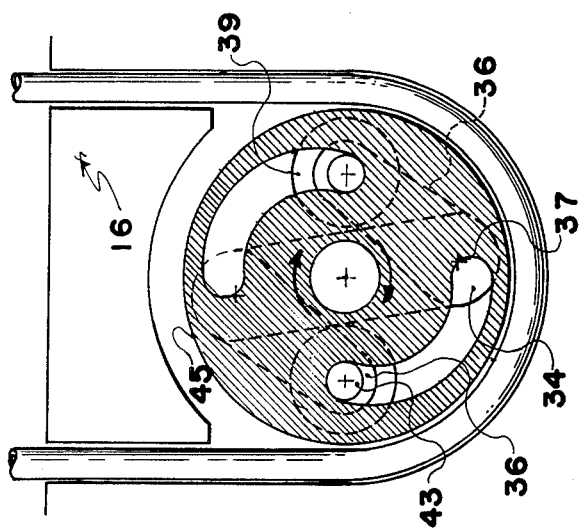
FIG. 10 is a partially cross sectioned schematic view of the roller assembly in the fully retracted position.

Machined into the undersurface of this disc are two cam shaped grooves 47 which mesh with the pins or sleeves 43 which protrude upward from pumping rollers 39. FIG. 10 shows the disc 12 in its extreme counter clockwise direction causing the pumping rollers to retract away from the tubing 15 and allowing space for the tube 15 to be inserted or removed freely into or from the groove recess. Fig. 11 shows the disc 45 rotated clockwise to an intermediate position where the pumping rollers are at their maximum distance from the rotor center. Resilience in the tubing allows a greater squeeze than required for optimum pumping. As the disc 45 is rotated manually clockwise still further towards its extreme position (FIG. 12), the cam shaped grooves 47 allow the pumping rollers to return slightly closer to the rotor center. In this position, the rollers are squeezing the tubing the proper amount for pumping. Resilience in the tubing exerts a moderate force which is transmitted through the pumping rollers 39 via the fixed pin or sleeve 43 located above each roller and meshing or engaging with the cam shaped grooves in disc 45. Due to the over-center shape of these grooves the disc is now inclined to rotate clockwise to its extreme position as shown in FIG. 12. The pumping rollers are now automatically locked at the proper distance from the rotor center for pumping and will retain this position until disc 45 is manually rotated counter clockwise. When in the position in FIG. 10, the sleeves 43 are at the ends 49 of the grooves and when in the position shown in FIG. 12, they are at the ends 50 of the grooves.

FIG. 10 shows the undialysed blood carrying tube 15 in the pump with the pumping rollers 39 fully retracted. While the rollers are retracted the tubing can be inserted into the pump or removed from it with ease. By manually rotating disc 45 clockwise approximately 90° (with reference to the drawings and in the direction of arrow 35), the pumping rollers 39 are forced against the tubing 15 and into position as shown in FIG. 12. With the rollers in this mode the pump can be operated with no possibility of the rollers changing distance from the center of the rotor.

This feature is unique in that no other pump combines retractable rollers (for ease of inserting tubing) while at the same time providing a preset radius about which the rollers revolve. The advantage of retractable rollers for ease of inserting tubing is apparent. With this pump, a simple twist of a serrated disc 45 changes roller position. No tools are required and the operator is not obliged to engage a separate lock to ensure that the roller position shall not change. The rollers are not spring loaded, thus allowing the operator to use both hands when inserting tubing. The preset fixed radius about which the rollers revolve is superior to a spring loaded feature found on some pumps in that an optimum roller pressure can be relied upon to minimize damage to blood cells while at the same time ensuring sufficient pressure to pump the blood efficiently.

Since the amount of squeeze on the tubing is very critical another feature has been incorporated into the design of the pump that allows a technician to adjust each roller independently. This compensates for slight machining irregularities. It also provides a means of adjusting roller pressure on the tubing to compensate for variation in tube size and wall thickness as can be seen in FIGS. 13 -16 as hereinbefore described.

Figure 8:
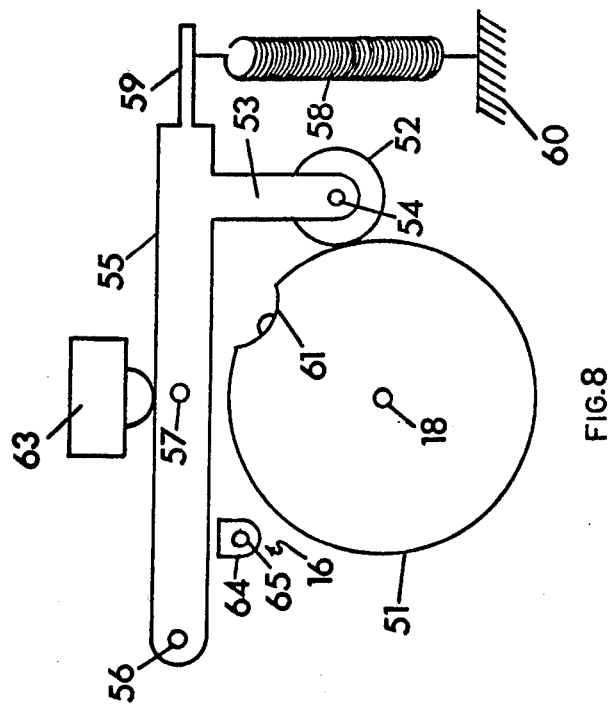
FIG. 8 is a partially schematic view of the occluder assembly per se.
Figure 5:
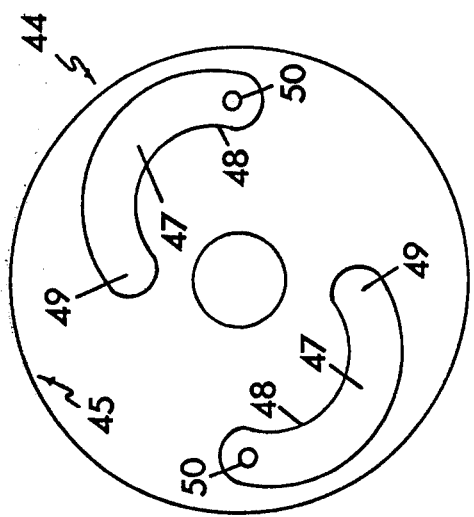
FIG. 5 is an underside view of the roller retracting member per se.

The occluding assembly generally designated 16 is shown in FIG. 4 and schematically in FIG. 8. A cam 51 is secured to the drive shaft below the upper plate 19 and engages a roller 52 journalled upon a projecting portion 53 by means of a mounting pin 54. The portion 53 offstands from the end of a lever 55 which in turn is pivoted to the underside of the upper plate 19 by means of pivot pin 56.

A cylindrical occluding pin 57 extends upwardly through the upper plate 19 and normally is situated within channel 26 thus engaging the dialysed blood carrying tube 14 with one wall of this channel 26 and closing off this tubing. However, a tension spring 58 extends between a lug 59 on one end of link 55, and a fixed part 60 of the casing and normally maintains the roller 52 in contact with the periphery of cam 51.

This cam is provided with a cut out portion 61 which, when the roller reaches same, enables the spring 58 to move the occluding pin into occluding engagement with tube 14 and out of a recess 62 opening out into the channel 26 as clearly shown in FIGS. 1, 3, 6 and 7.

A micro switch assembly 63 is also actuated by the movement of the lever or member 55 and this is operatively connected to the electric motor so that the motor is rotating while the roller 52 is being engaged by the major portion of the cam 51 but is switched off when the roller drops into the recess 61.

In operation, the flexible plastic tubes or conduits 14 and 15 are connected to the single needle 13 and to the dialysis machine 10 whereupon the member 45 is rotated to retract the rollers 39 away from the wall 29. The over-center action hereinbefore described, temporarily locks the rollers in the retracted position. This enables the tubing 15 to be laid in position around the wall 29 whereupon rotation of member 45 in the opposite direction, moves the rollers outwardly towards the wall in the operative or pumping position. Once again the over-center action sets and locks the rollers in the required relationship for the pumping action.

Tubing 14 is then laid into position, the occluding pin 57 being moved into the recess 62 by turning the drive shaft until the roller 52 is removed from the recess 61 of the cam 51. This can be undertaken by rotating the pump by means of the motor. The lid or cover is, of course, closed for this operation, to hold the tubes in position and to operate the interlock. In this regard, the lid or cover is preferably transparent to enable the operator to view the position of the occluding pin.

The power switch is then operated so that the rollers 39 rotate clockwise with respect to FIG. 6 in the mode illustrated in FIG. 6 under which circumstances the occluding pin 57 is clamping off the dialysed blood carrying tube 14. The rotation of the pump withdraws blood from the patient through the undialysed blood carrying tube 15 and forces same to the dialyser 10 until the roller 52 drops into the recess 61 on cam 51 at which time the occluding pin 57 is moved into the recess 62 due to the action of spring 58. This opens the dialysed blood carrying tube 14 and the pressure that has been build up in the dialyser forces the blood through this tube back to the patient. The timing sequence between the pumping mode and the non-pumping mode is controlled by means of a delay timer 64 and the speed of the pump is controlled by means of control 20 as hereinbefore described.

As an example, in FIG. 6, tubing 14 is closed off and the pump is rotating. As it rotates one revolution it draws approximately 8.5 ml of blood from the patient through the tube 15 and into the dialyser 10. The time for this part of the cycle is normally adjustable from between 1 and 10 seconds. An average time is 3 seconds. When the pump reaches the position shown in FIG. 7, the micro switch 63 is actuated thus stopping the pump and of course closing off tube 15. At the same time, the occluding pin 57 moves into the recess 62 thus releasing tube 14 and allowing dialysed blood to return to the patient. The time for this part of the cycle is also adjustable from between zero and 10 seconds, an average time being 3.5 seconds.

If the pump is to be used with a double needle system, then the occluder assembly 16 must be disabled as the pump operates continuously. One method of disabling the occluder assembly is illustrated in FIG. 8 which shows a cam 64 mounted upon a shaft 65 and engaging the underside of the lever 55. An operating knob or control 66 (see FIGS. 1 and 3) may be connected to the shaft 65 so that the cam can be rotated through 180°. When in the position shown in FIG. 8, the occluder assembly is operating, but if the cam is rotated through 180°, the lever or arm 55 is prevented from being pulled downwardly by spring 58 and roller 52 cannot enter the recess or notch 61.

It will also be appreciated that the time delay must be set to zero when used under these circumstances.

Figure 9:
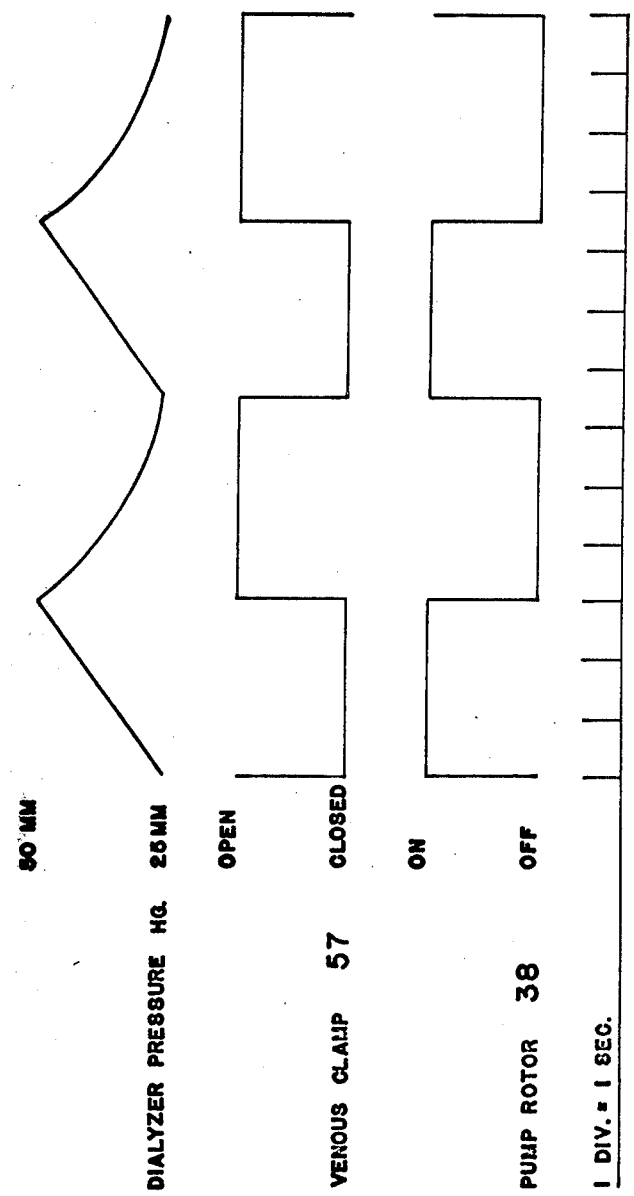
FIG. 9 shows a timing diagram of one selected status of the pumping sequence for single needle dialysis.

FIG. 9 shows a timing diagram of an arbitrarily selected set of conditions, with the device being used as part of a single needle dialysis system.

It will be appreciated that the present invention can be used with any presently used dialyser and that by its nature, it can be used for the treatment of acute or chronic cases as no time is lost in creating a fistula or other means for tapping off and returning blood to the patient.

Since various modifications can be made in our invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What we claim as our invention is:

1. In a dialysis pump for use with a conventional dialysis machine which includes a dialysed blood carrying flexible tube and an undialysed blood carrying flexible tube, a source of power, a shaft driven by said source of power, an upper plate, a dialysed blood carrying tube retaining channel formed in said upper plate and a curved undialysed blood carrying tube retaining wall also formed in said upper plate, a roller type pump assembly driven by said source of power and adapted to rotate against said undialysed blood carrying tube and collapse same against said wall, said pump including a pair of rollers journalled for rotation upon said drive shaft adjacent said wall to produce a pumping action within said undialysed blood carrying tube and an occluder assembly adapted to intermittently engage said dialysed blood carrying tube within its channel; the improvement comprising means to withdraw said rollers from said wall to facilitate engagement and disengagement of said undialysed blood carrying tube against said wall, said means including a rotor bar rotated by said source of power, means pivotally mounting said rollers adjacent the ends of said rotor bar in trailing relationship thereto, and manually operable means mounted upon the upper end of said drive shaft and cooperating with said rollers to retract same from said wall when rotated in one direction and to extend said rollers towards said wall when rotated in the other direction, said manually operated means including a member journalled for free rotation upon said drive shaft, means mounting said rollers for rotation and extending upwardly therefrom, an arcuately curved cam track channel for each of said last mentioned means, formed within the underside of said member and being slidably engageable by said means extending upwardly from said rollers, said cam track channels having inner and outer ends, rotation of said member in one direction when said pump is in the non-operating mode, moving said rollers to a retracted position relative to said wall and in the closest position to said drive shaft, rotation of said member in the opposite direction, moving said rollers to an extended position whereby said rollers are at the maximum distance from said drive shaft, and movement of said rollers further in said opposite direction to said outer ends of said channels, returning said rollers closer to said drive shaft, thereby detachably locking said rollers in the operating mode.

2. The device according to claim 1 in which said means pivotally mounting said rollers on said rotor bar includes a link for each roller pivotally secured by one end thereof to adjacent one end of said cross bar, said roller being mounted for rotation adjacent the other end of said link.

3. The device according to claim 1 which includes means to adjust the lateral distance of said rollers from said wall within limits, to control the pressure exerted by said rollers upon the wall of said undialysed blood carrying tube.

4. The device according to claim 2 which includes means to adjust the lateral distance of said rollers from said wall within limits, to control the pressure exerted by said rollers upon the wall of said undialysed blood carrying tube.

5. The device according to claim 3 in which said means to adjust the distance of said rollers from said wall includes adjustable eccentric means rigidly mounting said rollers upon the ends of said cross bar whereby the axis of rotation of said rollers can be shifted laterally towards or away from said wall in said upper plate.

6. The device according to claim 4 in which said means to adjust the distance of said rollers from said wall includes adjustable eccentric means rigidly mounting said rollers upon the ends of said cross bar whereby the axis of rotation of said rollers can be shifted laterally towards or away from said wall in said upper plate.

7. A dialyser pump for use with a conventional dialysing machine which includes a casing, a dialysed blood carrying flexible tube and an undialysed blood carrying flexible tube in said casing, said dialyser pump comprising in combination a source of power, a shaft driven by said source of power, an upper plate for said pump, a flexible dialysed blood carrying tube retaining channel formed in said upper plate and a curved undialysed blood carrying tube retaining wall also formed in said upper plate, a roller pump assembly driven by said source of power and adapted to rotate against said undialysed blood carrying tube to collapse same against said wall, said roller assembly including a pair of rollers pivoted for rotation upon said drive shaft, adjacent said wall, to produce a pumping action within said undialysed blood carrying tube, an occluder assembly adapted to intermittently engage said dialysed blood carrying tube within its channel, means to withdraw said rollers from said wall to facilitate engagement and disengagement of said undialysed blood carrying tube against said wall, said means including a rotor bar rotated by said source of power, means pivotally mounting said rollers adjacent the ends of said rotor bar in trailing relationship thereto and manually operated means mounted upon the upper end of said drive shaft and cooperating with said rollers to retract same from said wall when rotated manually in one direction and to extend said rollers towards wall when rotated manually in the other direction, said manually operated means including a member journalled for free rotation upon said drive shaft, means mounting said rollers for rotation and extending upwardly therefrom, an arcuately curved cam track channel for each of said last mentioned means, formed within the underside of said member and being slidably engageable by said means extending upwardly from said rollers, said cam track channels having inner and outer ends, rotation of said member in one direction when said pump is in the non-operating mode, moving said rollers to a retracted position relative to said wall and in the closest position to said drive shaft, rotation of said member in the opposite direction, moving said rollers to an extended position whereby said rollers are at the maximum distance from said drive shaft, and movement of said rollers further in said opposite direction to said outer ends of said channels, returning said rollers closer to said drive shaft, thereby detachably locking said rollers in the operating mode.

8. The device according to claim 7 in which said means pivotally mounting said rollers on said cross bar includes a link for each roller pivotally secured by one end thereof to adjacent one end of said cross bar, said roller being mounted for rotation adjacent the other end of said link.

9. The device according to claim 7 which includes means to adjust the lateral distance of said rollers from said wall within limits, to control the pressure exerted by said rollers upon the wall of said undialysed blood carrying tube.

10. The device according to claim 8 which includes means to adjust the lateral distance of said rollers from said wall within limits, to control the pressure exerted by said rollers upon the wall of said undialysed blood carrying 11. The device according to claim 9 in which said means to adjust the distance of said rollers from said wall includes adjustable eccentric means rigidly mounting said rollers upon the ends of said cross bar whereby the axis of rotation of said rollers can be shifted laterally towards or away from said wall in said upper plate.

12. The device according to claim 10 in which said means to adjust the distance of said rollers from said wall includes adjustable eccentric means rigidly mounting said rollers upon the ends of said cross bar whereby the axis of rotation of said rollers can be shifted laterally towards or away from said wall in said upper plate.

13. The device according to claim 7 which includes means to control the speed of said pump and hence the rate at which said pump operates.

14. The device according to claim 7 which includes a hinged cover for said upper plate and means cooperating with said cover for holding said tubes in position when said cover is closed, said last mentioned means including a retaining clip cooperating between said cover and said casing when said cover is closed and engaging said tubes and clamping said cover firmly in position.

15. The device according to claim 7 in which said occluder assembly includes an occluder pin means mounting said pin for movement into and out of engagement with the associated dialysed blood carrying tube within its channel.

16. The device according to claim 15 which includes means selectively to enable and disable said occluder assembly thereby changing said pump from a dual needle dialysis pump to a single needle dialysis pump and vice versa.

17. The device according to claim 7 which includes means to control the time of engagement and disengagement of said occluder assembly with said dialysed blood carrying tube within its channel.

* * * * *